United States Patent [19]

Zeineh et al.

[11] 4,014,610
[45] Mar. 29, 1977

[54] LINE LASER BEAM PRODUCTION AND ITS USE IN SCANNING DENSITOMETERS

[76] Inventors: Rashid A. Zeineh; William P. Nijm, both of 5742 W. Dakin St., Chicago, Ill. 60634

[22] Filed: Feb. 3, 1975

[21] Appl. No.: 546,514

[52] U.S. Cl. .......................... 356/201; 350/162 R
[51] Int. Cl.² ...................................... G01N 21/22
[58] Field of Search .......................... 350/201–203, 350/162 R, 162 SF; 356/201, 202, 203

[56] References Cited
UNITED STATES PATENTS 3,625,621  12/1971  Fields ................................ 356/201
3,802,784  4/1974  Reynolds et al. ................... 356/201
3,861,801  1/1975  Peters et al. ..................... 350/162 R

*Primary Examiner*—John K. Corbin
*Assistant Examiner*—Richard A. Rosenberger
*Attorney, Agent, or Firm*—McWilliams & Mann

[57] ABSTRACT

An arrangement for producing a laser beam as a line utilizing a sharp straight edge intercepting a portion of the original spot laser beam. The use of an diffraction grating at varying angles of the incident spot laser beam also produces a stretched laser spot of various orders with laser lines connecting the various orders.

4 Claims, 4 Drawing Figures

LINE LASER BEAM PRODUCTION AND ITS USE IN SCANNING DENSITOMETERS

BACKGROUND OF THE INVENTION

Many present scanners utilize tungsten light or other sources of white light. Colored or interference filters are usually used to produce monochromatic light. Fixed or adjustable slits produce a light beam of controlled width for scanning. Methods of separation, such as paper electrophoresis has improved greatly. Disc electrophoresis or isoelectric focusing has sharp resolution. The stained protein bands resolved by these techniques produces a complex pattern of closely stacked bands. Conventional scanners do not have compatible resolution for quantitative determination. Adjacent bands fuse together upon scanning.

Finer resolution is mainly obtained by utilizing a thinner light beam to scan with. A thinner light beam is produced by narrowing the slit that produces the beam. When the slit width gets to 0.10 millimeters or less the emerging beam produced by the slit diverges and the beam is wider than the slit. This limits the resolution of conventional scanners utilizing a white light source and a slit system to produce a thin light beam.

Using the phenomenom of laser, either the sharp edge or the filter technique produces a line laser of adjustable intensity. A segment of this line laser is taken and focused to a thinner beam by utilizing a cylindrical lens or mirror.

DETAILED DESCRIPTION OF THE DRAWINGS

Figure 1:
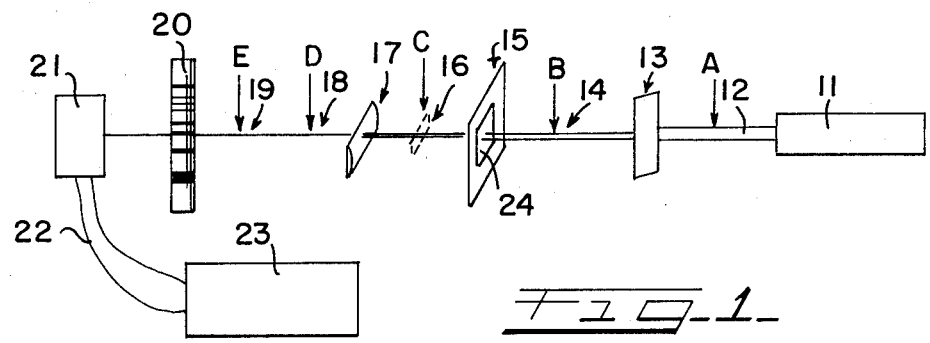
FIG. 1 illustrates the basic system to produce a thin laser beam with controlled intensity and adjustable width.

With specific reference to the drawings and referring to FIG. 1, the basis of utilizing laser light for densitometry is shown. The laser source 11 emits a laser light beam of spot type as at 12.

The sharp edge 13 is movable to intercept part of the laser beam 12, or to block it completely. When the edge 13 is partially intercepting the laser beam 12, the unintercepted beam 14 will have a cross sectional contour as indicated at B in FIG. 2. This cross section comprises a segment of a circle represented by the original laser beam before it has been affected by the sharp edge 13. If continued unchanged, the interference extension resulting from the effect of the sharp edge, its cross section appears as a very long generally triangular shape, represented schematically in FIG. 2. This portion of the beam extension is in continuity with the circular segment in beam 14 of FIG. 1 (cross section B of FIG. 2). This triangular extension resulting from diffraction effects produced by the sharp edge 13 with the laser beam is comprised of many interference spots as schematically represented in FIG. 3. These interference spots appear as a continuous light beam in the vicinity of the sharp edge 13. Restrictor or barrier 15 has an opening 24 that allows a part of the triangular extension beam B of FIGS. 1 and 2, to pass through as beam 16 of FIG. 1. Beam 16 is not broad in cross section and could be considered as the line portion of beam B of FIG. 2. Beam 16 is focused by cylindrical lens 17 (or by a cylindrical mirror, not shown) to a very narrow beam incident to object 20 that is to be scanned for densitometry or quantitation. The axis of the cylindrical lens 17 is in the same plane as beam 16. The separated bands in the object 20 are in the same plane, or parallel to such plane. The axis of the cylindrical lens 17 is perpendicular to the sharp edge 13. Photodetector 21 receives the transmitted light through the object and is relayed to electronic circuits 23 which comprise a recorder with mechanical attachments through a conduit 22. The electronic circuits, or recorder 23 process the entering impulses in the form desired. In some cases it provides numerical values as in colorimetry using cuvette and absorbing solutions. In densitometric scanning it usually provides a tracing on a chart recorder, with or without integrator and with or without computer printout or tracing.

Figure 2:
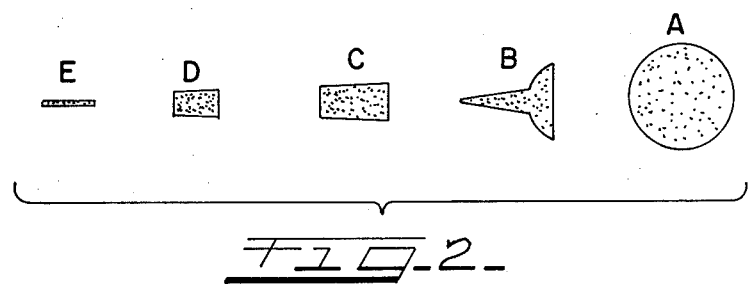
FIG. 2 is a cross section of the laser beam at various positions indicated in FIG. 1.
Figure 3:
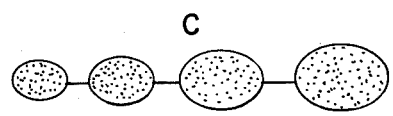
FIG. 3 is an enlarged representation of part C of FIG. 2.

FIG. 2 illustrates changes in laser beam. The original laser beam A—A, FIG. 1, a circular spot beam of Tempo mode usually. After the sharp edge provided at 24 has blocked part of the beam, the continued beam B, B—B FIG. 1 is more than a part or segment of the original beam which is a circular spot. An offshoot light beam in a form of a series of spot laser lights of various orders of interference that are very closely gathered form an apparent line laser beam. Beam B passes through opening 24, FIG. 1 and emerges as at C. Moving the straight edge back and forth perpendicular to the laser beam 12, FIG. 1 or as at A in FIG. 2, regulates that segment of the offshoot that goes through opening 24. Beam C is then focused by the cylindrical lens 17. Beam D at the position D—D of FIG. 1 is slightly compressed on the sides. It has the same length as at C, but has a smaller width than the beam at C. The focused beam E is further focused as it gets closer to the object 20 to be scanned. The beam length does not change, but its width is further compressed. Theoretically, the beam could be compressed to zero width at the object position 20. This attains maximal or infinite resolution. Moving the lens toward the object makes the focal point beyond the object and lower resolution is obtained. Moving the lens closer to the object makes the beam incident to the object wider, lowers resolution and increases sensitivity.

FIG. 3 illustrates the fine details of the offshoot of laser beam C at cross section C—C FIG. 1. The laser offshoot is really a series of elongated circles closely stacked together and probably connected by secondary offshoot of finer laser beam. These interference circles of the laser beam produced by the straight edge could be demonstrated against a screen a few feet distant from the straight edge. At close distance, such as in a densitometer embodiment, these elongated circles, or spots, appear as one continuous line. Upon focusing with the cylindrical lens, or mirror, they fuse together forming a more homogeneous line laser. The intensity is much less than the original laser beam. The intensity decreases as you get away from the blip end of the beam B, FIG. 2, as the beam width becomes narrower. Consequently, moving the straight edge back and forth vertically or perpendicular to the original beam 12, FIG. 1, produces and controls the focused beam C, FIG. 1, which is incident to the object during scanning.

Figure 4:
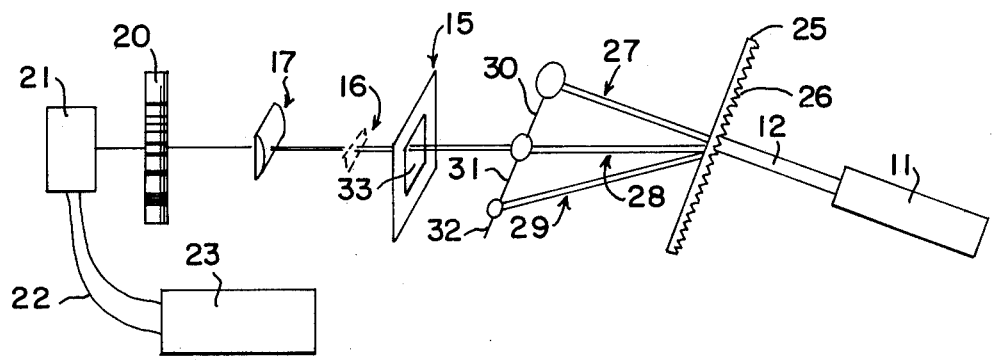
FIG. 4 illustrates the basic system of laser beam production utilizing an diffraction grating.

FIG. 4 illustrates the use of the diffraction grating to produce elongated spot laser beams of various orders and line laser beams connecting these orders. The laser tube 11 emits laser beam 12 which passes through an diffraction grating 25 with the grating 26 on one side, front or back, and the primary beam 27 is in the direction or continuation of the incident beam 12. Beam 27 does not change direction by rotating the filter 25. Beam 28 is the first order interference beam and 29 is in the second order. The offshoots 30, 31 and 32 etc. are line laser beams and rotating the filter results in moving the secondary beams, not the primary transmitted beam 27, and serves as selecting mechanism for any segment of the interference beams or offshoots to reach the cylindrical lens 17 passing through opening 33 in plate 15. The cylindrical lens, or its equivalent, the cylindrical mirror, will focus the transmitted beam and its offshoot or the reflected beams to a very thin line laser beam at the position of the object 20 to be scanned. Moving away from the primary transmitted beam the interference beams and the corresponding secondary offshoots get slimmer or decrease in width and also decrease in intensity. Thus the scanning resultant beam is controlled in intensity and in width.

What is claimed is:

1. A light source for a soft laser scanning densitometer/sphectrophotometer comprising a laser light source emitting a spot laser beam, a sharp edge movable to intercept part or all of the spot laser beam, the direction of said laser beam being perpendicular to the plane of said sharp edge and the movement of the sharp edge being in a plane perpendicular to the laser beam, a restrictor having an opening positioned in the path of the laser beam after said sharp edge, said restrictor opening passing a segment of that part of the laser beam produced by diffraction effects at said straight edge through a single cylindrical focusing means having its axis perpendicular to the sharp edge and in the path of said beam, said focusing means being positioned so that it focuses said laser beam to a thin line laser beam at an object to be scanned.

2. A light source for a soft laser scanning densitometer/spectrophotometer as set forth in claim 1 wherein said single cylindrical focusing means comprises a cylindrical lens which focuses transmitted light of said line laser beam on the object to be scanned.

3. A light source for a soft laser scanning densitometer/spectrophotometer as set forth in claim 1 wherein said single cylindrical focusing means comprises a cylindrical mirror which focuses reflected light of said line laser beam on the object to be scanned.

4. A light source for a soft laser scanning densitometer/spectrophotometer as set forth in claim 1 wherein said sharp edge movable in a direction perpendicular to the plane of the laser beam moves in a direction parallel to the axis of said cylindrical focusing means to change and control the intensity and width of the laser beam focused on said object.

* * * * *